(12) United States Patent
Piippo et al.

(10) Patent No.: US 8,162,964 B2
(45) Date of Patent: Apr. 24, 2012

(54) SPLIT FLEXIBLE TUBE BIASING AND DIRECTIONAL ATHERECTOMY DEVICE AND METHOD

(75) Inventors: Cassandra A. Piippo, Hugo, MN (US); Jesse C. Darley, Madison, WI (US)

(73) Assignee: Cardiovascular Systems, Inc., St. Paul, MN (US)

( * ) Notice: Subject to any disclaimer, the term of this patent is extended or adjusted under 35 U.S.C. 154(b) by 449 days.

(21) Appl. No.: 12/466,179

(22) Filed: May 14, 2009

(65) Prior Publication Data

US 2009/0306657 A1 Dec. 10, 2009

Related U.S. Application Data

(60) Provisional application No. 61/058,983, filed on Jun. 5, 2008.

(51) Int. Cl.
*A61B 17/22* (2006.01)
(52) U.S. Cl. .......................................... 606/159; 604/22
(58) Field of Classification Search .................... 606/45, 606/79, 108, 159, 170, 180; 604/22
See application file for complete search history.

(56) References Cited

U.S. PATENT DOCUMENTS

| | | | |
|---|---|---|---|
| 4,860,744 A * | 8/1989 | Johnson et al. ................. | 606/31 |
| 5,133,725 A | 7/1992 | Quadri | |
| 5,158,564 A | 10/1992 | Schnepp-Pesch et al. | |
| 5,360,432 A * | 11/1994 | Shturman ..................... | 606/159 |
| 5,411,514 A | 5/1995 | Fucci et al. | |
| 5,522,825 A | 6/1996 | Kropf et al. | |
| 5,624,455 A | 4/1997 | Matsuno | |
| 5,653,684 A | 8/1997 | Laptewicz et al. | |
| 5,843,103 A * | 12/1998 | Wulfman ...................... | 606/159 |
| 5,882,329 A | 3/1999 | Patterson et al. | |
| 5,902,263 A | 5/1999 | Patterson et al. | |
| 5,968,064 A | 10/1999 | Selmon et al. | |
| 5,984,939 A | 11/1999 | Yoon | |
| 6,146,395 A | 11/2000 | Kanz et al. | |
| 6,217,549 B1 | 4/2001 | Selmon et al. | |
| 6,398,798 B2 | 6/2002 | Selmon et al. | |
| 6,428,539 B1 | 8/2002 | Baxter et al. | |
| 6,508,825 B1 | 1/2003 | Selmon et al. | |
| 6,554,846 B2 | 4/2003 | Hamilton et al. | |
| 6,599,304 B1 | 7/2003 | Selmon et al. | |
| 6,638,247 B1 | 10/2003 | Selmon et al. | |
| 6,702,813 B1 | 3/2004 | Baxter et al. | |
| 6,746,451 B2 * | 6/2004 | Middleton et al. .............. | 606/79 |
| 6,746,462 B1 | 6/2004 | Selmon et al. | |
| 6,800,083 B2 | 10/2004 | Hiblar et al. | |

(Continued)

FOREIGN PATENT DOCUMENTS

EP 1158920 12/2005

*Primary Examiner* — Victor Nguyen
(74) *Attorney, Agent, or Firm* — Winthrop & Weinstine, P.A.

(57) ABSTRACT

The invention provides a rotational atherectomy system, device and method having a flexible, elongated, rotatable catheter tube that is split into two elements, a biasing element and a cutting element, distally and wherein the biasing element and cutting element are capable of forming a first and retracted position for insertion into a lumen and a second and expanded position for ablation. The biasing element is biased in the expanded position, thereby placing a biasing force against the lumen wall and pressing the cutting element against the opposite side of the lumen wall for directional cutting and/or grinding, either by rotation, axial translation, vibration or a combination thereof.

22 Claims, 2 Drawing Sheets

U.S. PATENT DOCUMENTS

| | | |
|---|---|---|
| 6,800,085 B2 | 10/2004 | Selmon et al. |
| 7,033,357 B2 | 4/2006 | Baxter et al. |
| 2003/0060685 A1 | 3/2003 | Houser et al. |
| 2005/0192606 A1 | 9/2005 | Paul et al. |
| 2007/0129740 A1 | 6/2007 | Schwartz et al. |
| 2008/0114364 A1 | 5/2008 | Goldin et al. |

* cited by examiner

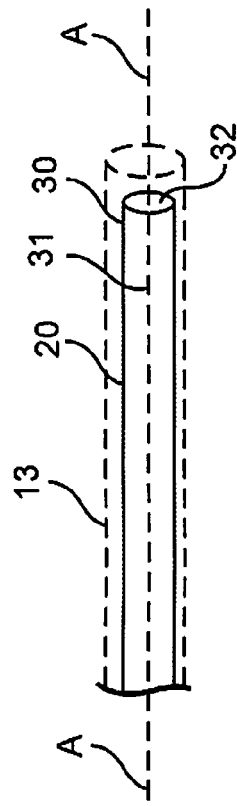
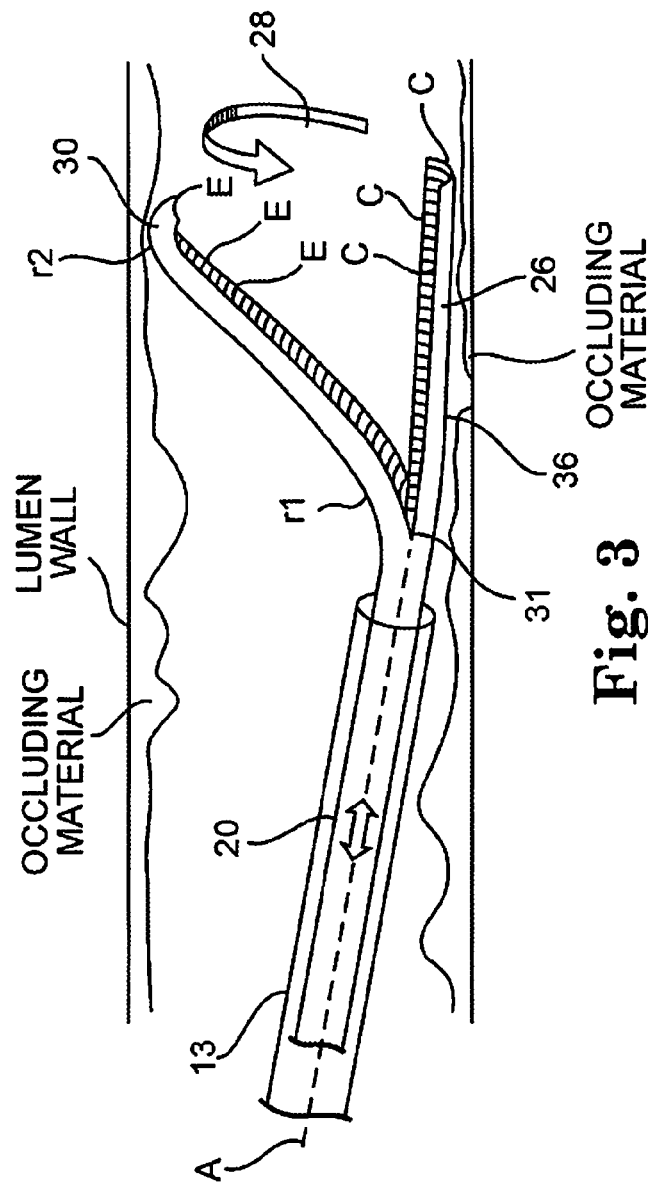

SPLIT FLEXIBLE TUBE BIASING AND DIRECTIONAL ATHERECTOMY DEVICE AND METHOD

CROSS-REFERENCE TO RELATED APPLICATIONS

The present application claims priority to provisional application No. 61/058,983, filed on Jun. 5, 2008 under the title, "SPLIT FLEXIBLE TUBE DIRECTIONAL LARGE VESSEL ATHERECTOMY DEVICE", the contents of which are incorporated by reference herein.

BACKGROUND OF THE INVENTION

1. Field of the Invention

The invention relates to devices and methods for removing tissue from body passageways, such as removal of atherosclerotic plaque from arteries, utilizing a rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic or occluding material. If left untreated, this occluding material can cause angina, hypertension, myocardial infarction, strokes and the like.

Rotational atherectomy procedures have become a common technique for removing such occluding material in blood vessels. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove occluding material. In one type of device, such as that shown in U.S. Pat. No. 4,990,134 (Auth), a concentrically shaped ellipsoidal burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently, since the burr is of a fixed resting diameter, more than one size burr must be utilized to open an artery to the desired diameter.

U.S. Pat No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., rotational speeds within the range of about 20,000-200,000 rpm. Essentially, the center of mass offset from the rotational axis of the drive shaft would result in development of significant and undesirable centrifugal force, exerting too much pressure on the wall of the artery and creating too much heat and excessively large particles. As with Auth, the burr size is fixed and may require using more than one size burr to open the subject lumen to the desired diameter.

U.S. Pat. No. 6,132,444 (Shturman) and U.S. Pat. No. 6,494,890 (Shturman) both commonly assigned, disclose, inter alia, an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The orbital rotational motion is primarily due to the offset of the center of mass of the enlarged eccentric section from the drive shaft's rotational axis. Since the enlarged eccentric section may comprise drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. The disclosure of U.S. Pat. Nos. 6,132,444 and 6,494,890 are each hereby incorporated by reference in their entirety.

Other techniques and devices have been proposed to generate a rotational sweeping diameter that is greater than the resting diameter of the abrasive section. Generally, these devices include a pre-bent guide wire that will, when placed within the lumen of a rotational drive shaft, create a bend in the drive shaft at the abrasive region. When the guide wire is removed, the drive shaft returns to its normal uncurved and substantially linear shape. Such an arrangement will, when the pre-bent guide wire is in place, create a sweeping diameter for the abrasive region of the drive shaft that is greater than its resting diameter. Examples of such pre-bent guide wire proposals include U.S. Pat. Nos. 5,312,427, 5,356,418, 5,554, 163 all to Shturman and commonly assigned with the present application, the disclosure of each being incorporated herein by reference insofar as they disclose a drive shaft is urged into a curvilinear profile by virtue of the presence of the curved guide wire within the drive shaft's lumen. Other examples include U.S. Pat. No. 5,548,843 to Wulfman and U.S. Pat. No. 6,156,046 to Passafaro. These pre-curved guide wire designs are not, inter alia, capable of providing a controllable biasing force on one side of the lumen for directional cutting and/or grinding occluding material on the other side of the lumen.

A number of attempts to expand the radial reach of rotational cutting and/or grinding/sanding elements have been proposed. For example, U.S. Pat. No. 5,158,654 to Schnepp-Pesch discloses a cutting element with two expanding outwardly biased ends having distal and radial cutting elements. This cutting element may thus provide tissue cutting action when advanced and/or rotated. Schnepp-Pesch does not, however, provide directionality of cutting nor does it provide a controllable biasing force on one side of the lumen for directional cutting and/or grinding occluding material on the other side of the lumen.

Pending U.S. Patent Application 2008/0114364 to Goldin discloses a medical device for forming or modifying cavities in tissue including a blade extendable laterally from a first shape to a second shape. Each embodiment disclosed by Golden requires a lateral aperture, wherein the lateral aperture is provided in the insertion tube and is operably configured to accept passage of the second shape of the flexible cutting element therethrough. Golden's cutting element is biased radially to engage subject tissue. Goldin does not, however, provide a controllable biasing force on one side of the lumen for directional cutting and/or grinding occluding material on the other side of the lumen.

U.S. Pat. Nos. 6,217,549, 6,398,798, 6,508,825, 6,746,462, 6,638,247, 6,599,304, 5,968,064, 6,800,085 all to Selmon disclose a hinged spreading member at the distal end of a catheter for exerting substantially lateral distal end forces on the region surrounding an occluded blood vessel. The spreading or tissue expansion members may stretch, tear or otherwise disrupt (fracture) the occlusion sufficiently to create a pathway that may support the passage or placement of a guidewire or interventional vascular device. Selmon's patents do not, however, provide directionality of cutting and/or grinding of occluding material nor do they provide a controllable biasing force on one side of the lumen for directional cutting and/or grinding of occluding material on the other side of the lumen Finally, U.S. Pat. Nos. 5,882,320 and 5,902,263, both to Patterson disclose displacing a shearing body with a stented region to dislodge stenotic material from the inner surface of the stent. Patterson's patents do not, however, provide directional cutting and/or grinding nor do they provide a controllable biasing force on one side of the lumen for directionality of cutting and/or grinding on the other side of the lumen Thus, it would be highly advantageous to provide an atherectomy system, device and method that allows for provision of directionality of cutting via exertion of a controllable biasing force against the lumen with directional cutting on the other side of the lumen. It would be further advantageous to provide an atherectomy system, device and method that may be rotated to achieve cutting and/or grinding. It would be further advantageous to provide an atherectomy system, device and method that may be manually advanced axially and/or vibrated to achieve cutting and/or grinding.

The present invention addresses, inter alia, these needs.

BRIEF SUMMARY OF THE INVENTION

The invention provides a rotational atherectomy system, device and method comprising a flexible, elongated, rotatable catheter tube that is split into two elements, a biasing element and a cutting element, distally and wherein the biasing element and cutting element are capable of forming a first and retracted position for insertion into a lumen and a second and expanded position for ablation. The biasing element is biased in the expanded position, thereby placing a biasing force against the lumen wall and pressing the cutting element against the opposite side of the lumen wall for directional cutting and/or grinding, either by rotation, axial translation, vibration or a combination thereof.

An object of the invention is to provide an atherectomy device with a small crossing profile, i.e., less than 6 French, but that also can fully ablate occluding material in vessels having diameters of up to 9 mm.

Another object of the invention is to provide an atherectomy device that comprises a first retracted position for insertion into vasculature and a second expanded position for ablation.

Another object of the invention is to provide an atherectomy device that provides a biasing force to allow for directional ablation within a lumen.

Another object of the invention is to provide an atherectomy device comprising a rotational catheter tube comprising a biasing element and a cutting element.

Another object of the invention is to provide an atherectomy device comprising a biasing element that, when released, automatically expands to the lumen wall to exert a biasing force.

Another object of the invention is to provide an atherectomy device comprising a cutting element that is biased against target occluding material.

Another object of the invention is to provide an atherectomy device comprising a cutting element that may cut occluded material when rotated and/or axially translated.

Another object of the invention is to provide an atherectomy device comprising a cutting element that may cut and/or grind occluding material when rotated and/or axially translated.

Another object of the invention is to provide an atherectomy device comprising a cutting element that may cut and/or grind occluding material when rotated and/or axially translated when subjected to ultrasonic forces.

Another object of the invention is to provide an atherectomy device comprising a cutting element that is formed to protect healthy tissue from trauma during the atherectomy procedure.

Another object of the invention is to provide a system and methods to achieve, inter alia, the above objectives.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

FIG. 2 is a cutaway side view of one embodiment of the present invention.

FIG. 3 is a cutaway side view of one embodiment of the present invention.

DETAILED DESCRIPTION OF THE INVENTION, INCLUDING THE BEST MODE

Figure 1:
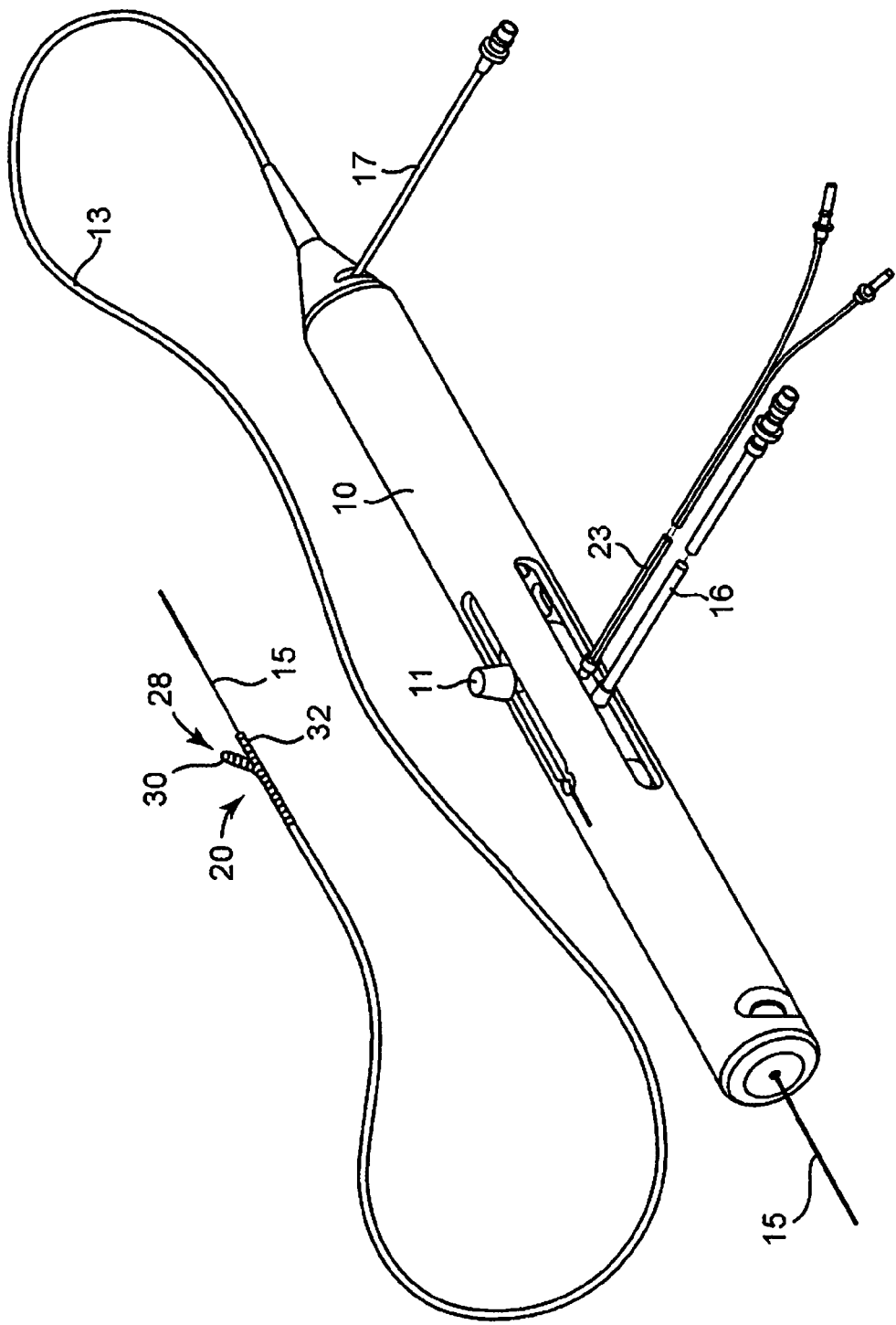
FIG. 1 is a perspective view of one embodiment of the present invention.

While the invention is amenable to various modifications and alternative forms, specifics thereof are shown by way of example in the drawings and described in detail herein. It should be understood, however, that the intention is not to limit the invention to the particular embodiments described.

On the contrary, the intention is to cover all modifications, equivalents, and alternatives falling within the spirit and scope of the invention.

FIG. 1 illustrates one embodiment of a rotational atherectomy system and device of the present invention. The system includes a handle portion 10, an elongated, flexible catheter tube 20 having an ablating element 28 which further comprises a biasing element 30 and a cutting element 32, the biasing element 30 and the cutting element 32 resulting from, in the illustrated embodiment, a splitting of the flexible catheter tube 20 at its distal end. Flexible catheter tube 20 comprises a lumen with which guide wire 15 may be in operative communication. The device and system is illustrated with guide wire 15 in position, however, the skilled artisan will recognize that atherectomy procedures using the present invention may be completed satisfactorily either with or without guide wire 15 extended through ablating element 28. Moreover, catheter tube 20 is in rotatable and axially translatable and operative communication with introducer catheter 13 and introducer catheter's lumen. The ablating element 28 is illustrated as radially extending distally from introducer catheter 13, wherein the catheter tube 20 and the introducer catheter 13 are translated axially relative to one another. This relative axial translation may be achieved by pushing the catheter tube 20 distally, pulling the introducer catheter 13 proximally, or a combination thereof. Thus, the biasing element 30 is illustrated in its undeformed and expanded position, having moved radially outwardly away from its deformed and retracted position adjacent with cutting element 32.

A fluid supply line 17 may be provided for introducing a cooling and lubricating solution (typically saline or another biocompatible fluid) into the catheter 13 wherein fluid supply line is operatively connected with catheter. In certain embodiments warming and/or cooling biocompatible fluid may be introduced and/or urged into the catheter 13 via fluid supply line.

The handle 10 desirably contains a turbine (or similar rotational drive mechanism) for rotating the catheter tube 20 at very low to relatively high speeds in a single rotational direction, and is further capable of rotating catheter tube 20 in the opposing rotational direction and/or in reciprocating rotational directions. The handle 10 typically may be connected to a power source, such as compressed air delivered through a tube 16. A pair of fiber optic cables 23 may also be provided for monitoring the speed of rotation of the turbine and catheter tube 20 (details regarding such handles and associated instrumentation are well known in the industry. The handle 10 also desirably includes a control knob 11 for advancing and retracting the turbine and catheter tube 20 with respect to the catheter 13 and the body of the handle 10.

Debris created during the ablation using cutting element 28 may be captured by a suction applied within the lumen of catheter tube 20. Alternatively, such debris may be captured distal to the ablation site using known distal embolic protective devices.

As used herein, the term "ablation" shall mean cutting and/or grinding as a result of side-to-side motion, rotational motion, reciprocating rotational motion, forward and/or backward motion, i.e., proximal and/or distal motion, whether resulting from manual, automated, motorized and/or vibrational means.

With reference now to FIG. 2, one embodiment of the present invention is illustrated with ablating element 28 in a first, deformed and retracted position. In this retracted position, the biasing element 30 and the cutting element 32 are within the lumen of introducer catheter 13 and collinear with longitudinal axis A. As illustrated, biasing element 30 and cutting element 32 are in a closed retracted position, collapsed against and adjacent to one another to obtain a profile that is comparable with that of catheter tube 20 proximal to the longitudinal split 31, whereby biasing element 30 and cutting element 32 are created. Thus, in this embodiment, the distance between the inner diameter of introducer catheter 13 and the outer diameter of ablating element 28 when retracted is relatively small as will be readily understood by the skilled artisan, while still allowing the rotatability and axial translatability between introducer catheter 13 and catheter tube 20 required by the present invention. In practice, the preferred embodiment of catheter tube 20 and ablating element 28 in the retracted position will fit within the lumen of a 6 French introducer tube 13. This retracted position thus allows the ablating element 28 to be positioned via introducer tube 13 near occluding material without causing unnecessary trauma during insertion via the patient's vasculature.

FIG. 3 illustrates one embodiment of the present invention with ablating element 28 in a second, undeformed and expanded position. In this expanded position, the biasing element 30 and the cutting element 32 are moved distally from the lumen of introducer catheter 13, wherein biasing element 30 automatically opens to move toward its undeformed shape and profile and away from cutting element 32 and longitudinal axis A. Cutting element 32 remains substantially collinear with the longitudinal axis A, though cutting element 32 is flexible and, as a result, may bend slightly to conform with the vessel landscape and requirements of the procedure.

As the ablating element 28 is positioned distally outwardly beyond the constricting lumen of introducer catheter 13, the biasing element 30 experiences an elastic and non-plastic deformation to achieve the expanded position within the subject lumen. As discussed briefly above, the expanded diameter of the biasing element 30 and cutting element 32 in the expanded position is sufficient to accommodate vessels having diameters as large as 9 mm. Thus, the biasing element 30 is preferably constructed so that, when released from deformation, it automatically moves to assume a position that is in a pressing and atraumatic operative engagement with the inner lumen wall. Cutting element 32 remains substantially collinear with longitudinal axis A.

Thus, at least a portion of the outer surface 36 of biasing element 30 operatively presses against the inner wall of the lumen. This creates an opposing biasing force that is transmitted to, and ultimately exerted by, the outer surface 36 of cutting element 32 against the inner wall of the lumen, preferably in close proximity to the occluding material that is to be directionally ablated. In this manner, the cutting element 32 is biasingly forced against the inner wall of the lumen in preparation for directional ablation, i.e., cutting and/or grinding.

As illustrated, the outer surface 36 of biasing element 30 is relatively smooth and provides an atraumatic surface for pressing engagement with the lumen wall. This atraumatic surface is further enabled by the half-circle profile of biasing element 30 embodiment shown, resulting from the substantially equal splitting of catheter tube 20 as shown. Furthermore, the shaping memory material and process, discussed further below, may provide an undeformed shape which further supports pressing biasing force by biasing element 30. For example, one or more curvilinear radii may be formed into the biasing element 32, shown illustratively as r1 and r2. These curvatures, together with the generally and preferably circular profile of ablating element 28 and, therefore, of biasing element 30, effectively moves the edges E of biasing element 30 away from any healthy tissue. In this manner the possibility of biasing element cutting or grinding or otherwise causing trauma to any tissue is effectively eliminated. All ablation, i.e., cutting and/or grinding, is achieved with the cutting element 32 in a directionally focused manner.

The cutting element 32 also comprises a radiused profile, illustrated as a half-circle and complementary in profile to that of biasing element 30, since the tube is split approximately in half, though other configurations are within the scope of this invention. The radiused profile of cutting element 32, provides cutting edges C along the sides of cutting element 32 for rotating cutting as well as cutting edge C along the distal end of cutting element 32 for axial translating cutting. Such cutting edges C may comprise a sharpened edge as will be readily understood by the skilled artisan. Alternative embodiments comprise cutting edges that may be serrated or contain cutting barbs, razors, abrasive and/or beveled surfaces to facilitate cutting of occluding material. Further, the outer surface 36 of cutting element 32 may comprise an abrasive material 26 coated thereon, e.g., diamond dust, or may comprise a roughened abrasive surface as is well known in the art.

The skilled artisan will recognize that the profiles of biasing element 30 and cutting element 32 need not necessarily be complementary in the sense that the edges E and C close substantially directly together when in the retracted position. Alternative embodiments may comprise the cutting element comprising a larger radiused profile than that of biasing element 30, wherein retraction of biasing element 30 and cutting element 32 results in the respective edges E and C being held within lumen of introducer sheath 13 adjacent one another rather than held substantially together in direct contact as illustrated. Such an alternate arrangement may allow for more effective cutting since the cutting edges C will be lowered and closer to the occluding material to be cut and/or ground by ablating element 28.

Moreover, the structure of ablating element 28 is illustrated as generally circular in transverse cross section. This is a preferred cross-sectional profile, however alternate shapes and profiles may present themselves to those skilled in the art. For example, elliptical, rectangular, square, and polygonal transverse cross-sectional profiles may be used with success for the ablating element 28 and with the biasing element 30 and/or cutting element 32. Each such alternate embodiment is within the scope of the present invention.

In all embodiments of the cutting element 32, abrasive 26 may be coated onto outer surface 36 of cutting element 32. By way of example, the abrasive material may be any suitable material, such as diamond powder, fused silica, titanium nitride, tungsten carbide, aluminum oxide, boron carbide, or other ceramic materials. The abrasive material may comprise diamond chips (or diamond dust particles) attached and/or coated directly to the outer surface 36, such attachment may be achieved using well known techniques, such as conventional electroplating or fusion technologies (see, e.g., U.S. Pat. No. 4,018,576). Alternately the outer surface 36 may comprise an external tissue removing surface which has been roughened to provide a suitable abrasive surface. In yet another variation, the external surface may be etched or cut (e.g., with a laser) to provide small but sharp cutting surfaces. Other similar techniques may also be utilized to provide a suitable tissue removing surface for outer surface 36.

In the illustrated embodiment, the abrasive outer surface 36 may be used to grind during rotation of the cutting element 32 and/or during axial translation of the cutting element 32.

The biasing element 30 is preferably flexible and may be constructed from virtually any material capable of elastic characteristics, but operating within the selected material's range of elastic and non-plastic deformation. Preferably, shape memory materials such as Nitinol may be used to achieve the desired shaping of biasing element 30 in a manner well known to the skilled artisan. Releasing the biasing element 30 from constriction within, e.g, the introducer tube 13 allows the biasing element to automatically resume its non-deformed and shaped form.

Examples of superelastic metal alloys, including Nitinol, which are usable to form certain embodiments of the biasing element 30 of the present invention are described in detail in U.S. Pat. No. 4,665,906. The disclosure of U.S. Pat. No. 4,665,906 is expressly incorporated herein by reference insofar as it describes the compositions, properties, chemistries, and behavior of specific metal alloys which are superelastic within the temperature range at which the biasing element 30 of the present invention operates, any and all of which superelastic metal alloys may be usable to form the biasing element 30.

As shown, there is one longitudinal split 31 in the ablating element 28 which may comprise a generally circular cross-section when in retracted position, thus creating one radiused biasing element 30 and one radiused cutting element 32. Various alternate embodiments may be created as will be readily understood by creating a cutting element that comprises more than one longitudinal split. In this manner, more than one biasing element 30 may be provided to provide more biasing force for the cutting element 32 against the occluding material. Alternatively, more than one cutting element 32 may be provided. Still more alternatively, more than one cutting element 32 and more than one biasing element 30 may be provided.

In addition to the constriction and release of the biasing element 30 formed from shape memory alloy from the lumen of introducer catheter 13, controlled application of heating and cooling methods may be used to induce the biasing element 30 to deform to substantially linear retracted position or undeform to its radially expanded position. Thus, the operator may apply heat to the biasing element 30 by bathing the biasing element 30 in a heated and/or heat-controlled (heatable and/or coolable) physiologically compatible fluid (e.g., saline, Ringer's Solution, etc.) that is introduced via the lumen of introducer catheter 13 and/or through the lumen of catheter tube 20. By controlling the temperature of the fluid introduced, either warming or cooling, the temperature of the biasing element 30 is similarly controlled to affect its shape in urging the biasing element 30 to/from retracted position to expanded position and back to retracted position.

Alternatively, the operator may control the retracted versus expanded position of biasing element 30 by controlling the temperature of biasing element 30 by passing current through the guide wire 15 from its proximal end to allow the biasing element 30 to controllably achieve its undeformed and expanded position due to the heat generated in biasing element 30 by the current applied as described. Alternatively, a cooling effect may be realized by using a Peltier device as is well known in the art to return the biasing element 30 to its deformed and retracted position. As those skilled in the art will recognize, the application of electrical current to biasing element 30 may be accomplished by attaching one or two leads operatively connected with biasing element 30.

The structure of the present invention having been described in detail, we now turn to discussion of methods of use of the present invention and its operation.

The procedure may begin with inserting a guide wire 15 to a position proximate the occluding material. An introducer catheter 13 may be provided with guide wire 15 within lumen of introducer catheter 13, to a position proximal the occluding material. The guide wire 15 may be withdrawn and catheter tube 20 may be introduced through introducer catheter's 13 lumen. Catheter tube 20 comprises the ablating element 28 of the present invention, including biasing element 30 and cutting element 32. When ablating element 28 is retained within catheter tube 20 lumen, it will be in retracted position, with biasing element 30 in a deformed substantially linear alignment with longitudinal axis A.

The ablating element 28 may be extended distally from the confines of the lumen of introducer catheter 13 which may result in automatic expansion of biasing element 30 to pressingly and atraumatically engage the inner lumen wall.

Simultaneously, the cutting element 32 is experiencing a pressing force against the inner wall of the lumen opposite that of the biasing member's 30 pressing engagement. The operator may either position the cutting element 32 by rotation and translation prior to expanding ablating element 28 or after expansion.

When the expanded position is achieved, the operator may rotate the ablating element 28, resulting in engagement of the occluding material by the cutting edge(s) C of cutting element 32. Further, abrasion may occur as a consequence of the abrasive outer surface 36 being pressed against the occluded material during rotation.

Such rotation may occur at very low to reasonably high rotational speeds enabled by the apparatus of FIG. 1, or the operator may rotate the ablating element 28 by hand. Alternatively, manual or automated reciprocating rotational and/or axial movement may allow focused directional ablation of a specific region of the subject lumen and/or allow biased ablation of the entire circumference of the subject lumen. Alternative reciprocating methods may comprise rotational reciprocation of less than one full revolution or rotational reciprocation of one full revolution or rotational reciprocation of more than one full revolution.

Further, the operator may move the expanded ablating element 28 axially, proximally and/or distally, to engage the distal cutting edge C of cutting element 32 to enhance the ablating process. This axial movement may be achieved by manual proximal and/or distal movement of the ablating element 28 and/or by high-frequency vibration provided by, e.g., a piezo motor in operative communication with ablating element 28 as will be well understood by the skilled artisan. Automated axial movement may be achieved using motorized devices well known to the skilled artisan for applying force in a distal direction on the ablating element 28. Automated axial reciprocating movement, i.e., alternating application of proximal and distal force, may also be used. Alternatively, a piezo actuator may be positioned near the ablating element 28 and in operative communication with a conductive wire which energizes the piezo actuator, there by causing the actuator to change length at a high frequency and resulting in high-frequency vibration and axial movement of cutting element 32 through occluding material. Such piezo actuator may, for example, be operationally connected with the catheter tube 20, effectively creating a piezotube for high-frequency vibration of the ablating element 28 and cutting element 32. Such vibrational cutting action is not limited to axial movement of cutting element 32. The side cutting edges C of cutting element 32 may be induced to cut soft tissue when vibrated side to side at a high frequency by the well-known piezo mechanisms discussed supra.

Throughout the procedure, the biasing element 30 maintains an opposing biasing force that presses the cutting element 32 against the occluding material.

When the occluding material is sufficiently cleared away, the operator may then retract the expanded ablating element 28 proximally into the lumen of introducer catheter 13, thus retracting ablating element 28 to its retracted position for withdrawal from the patient.

Alternatively, the introducer catheter 13 may not be required in the embodiment where the expanded and retracted positions of the ablating element 28 are achieved using alternating heating and cooling, i.e., either by perfusion of controlled temperature liquid, e.g., saline, or by application of electrical current.

Thus, a method of directionally clearing target tissue comprising occluding material within a lumen using the present invention may comprise:

providing a catheter tube having an outer diameter smaller than the lumen and having an ablating element in a deformed retracted position at the distal end of the catheter tube;

advancing the catheter tube through the lumen to a position proximate the occluding material;

urging the deformed retracted ablating element into an undeformed expanded position;

allowing the ablating element's biasing element to atraumatically engage the inner lumen wall while forcing the ablating element's cutting element against the occluding material;

directionally ablating the occluding material while avoiding healthy tissue within the lumen;

urging the expanded ablating element into its deformed retracted position; and withdrawing the retracted ablating element from the lumen.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A directional rotational atherectomy device for directional biasing ablation of occluding material in a blood vessel having a given diameter, comprising:
    a rotatable catheter tube having an outer diameter less than the diameter of the blood vessel and a lumen therethrough and further comprising a distal end, the distal end comprising a longitudinal split, and a longitudinal axis;
    an ablating element formed from the longitudinal split of the distal end of the catheter tube, comprising at least one biasing element, and at least one cutting element, the ablating element comprising an undeformed expanded position and a deformed retracted position, wherein the deformed retracted position comprises the at least one cutting element having a position that is substantially collinear with the catheter tube longitudinal axis and the at least one biasing element deformable to a position substantially collinear with the catheter tube longitudinal axis and adjacent with the at least one cutting element, and wherein the undeformed expanded position comprises the at least one cutting element having a position that is substantially collinear with the catheter tube longitudinal axis and the at least one biasing element undeformed and radially expanded away from the at least one cutting element.

2. The rotational atherectomy device of claim 1, further comprising an insertion catheter having a lumen, the rotatable catheter tube in operational communication with the insertion catheter lumen, wherein the ablating element is held in the deformed retracted position by the insertion catheter lumen and automatically expands to the undeformed expanded position when the ablating element is not confined by the insertion catheter lumen.

3. The rotational atherectomy device of claim 1, at least one biasing element comprising a shape memory alloy.

4. The rotational atherectomy device of claim 3, further comprising wherein the expanded undeformed position is achieved automatically.

5. The rotational atherectomy device of claim 4, wherein the at least one biasing element comprises one or more curvilinear radii formed into the biasing element.

6. The rotational atherectomy device of claim 3, wherein the undeformed expanded position is achieved by increasing the temperature of the ablating element.

7. The rotational atherectomy device of claim 3, wherein the deformed retracted position is achieved by decreasing the temperature of the ablating element.

8. The rotational atherectomy device of claim 1, further comprising cutting edges on the at least one cutting element.

9. The rotational atherectomy device of claim 1, wherein the at least one cutting element comprises an outer surface having abrasive coated thereon.

10. The rotational atherectomy device of claim 1, wherein the expanded position of the at least one biasing element comprises the at least one biasing element being offset from the longitudinal axis of the catheter tube.

11. The rotational atherectomy device of claim 1, wherein the retracted position of the ablating element comprises a diameter of 6 French.

12. The rotational atherectomy device of claim 1, wherein the expanded position of the ablating element comprises a diameter of 9 mm.

13. The rotational atherectomy device of claim 1, further comprising a piezo device in operative communication with the ablating element, wherein actuation of the piezo device results in ablation by high-frequency vibration of the ablating element.

14. The rotational atherectomy device of claim 1, wherein ablation occurs by rotation and/or axial translation of the expanded ablating element.

15. The rotational atherectomy device method of claim 14, wherein the directional ablation further comprises manual rotation and/or axial translation, automated rotation and/or axial translation, and/or motorized rotation and/or axial translation.

16. The rotational atherectomy device of claim 15, wherein the automated rotation and/or axial translation comprises reciprocating rotation and/or axial translation.

17. A method of directionally ablating occluding material within a lumen comprising:

providing a catheter tube having an outer diameter smaller than the lumen longitudinal axis, and having an ablating element comprising a biasing element and a cutting element in a deformed retracted position at the distal end of the catheter tube the distal end of the catheter tube comprising a longitudinal split, wherein the biasing element and cutting element are positioned adjacent each other and substantially collinear with the longitudinal axis of the catheter tube;

advancing the catheter tube through the lumen to a position proximate the occluding material;

urging the deformed retracted ablating element into an undeformed expanded position, whereby the biasing element radially expands away from the cutting element while the cutting element remains substantially collinear with the longitudinal axis of the catheter tube;

allowing the ablating element's biasing element to atraumatically engage the inner lumen wall while forcing the ablating element's cutting element against the occluding material;

directionally ablating the occluding material while avoiding healthy tissue within the lumen;

urging the expanded ablating element into its deformed retracted position; and withdrawing the retracted ablating element from the lumen.

18. The method of claim 17, further comprising:
providing a piezo device in operative communication with the ablating element;
vibrating the ablating element at high-frequency to ablate occluding material.

19. The method of claim 17, further comprising:
applying heat to urge the deformed retracted ablating element into an undeformed expanded position; and
cooling the ablating element in its undeformed expanded position to urge the ablating element into its deformed retracted position.

20. The method of claim 19, further comprising flushing the pre-curved section with a temperature controlled biocompatible solution to urge the ablating element into its undeformed expanded position and its deformed retracted position.

21. The method of claim 18, further comprising using electrical current to urge the ablating element into its undeformed expanded position and its deformed retracted position.

22. The method of claim 21, further comprising using a Peltier device to urge the ablating element from its undeformed expanded position into its deformed retracted position.

* * * * *